(12) United States Patent  
Cornish et al.

(10) Patent No.: US 8,431,667 B2  
(45) Date of Patent: Apr. 30, 2013

(54) GUAYULE NATURAL RUBBER LATEX THIN FILM ARTICLES

(75) Inventors: Katrina Cornish, Casa Grande, AZ (US); Jali Williams, Phoenix, AZ (US); Kc Nguyen, Maricopa, AZ (US); Brian Fishman, Chandler, AZ (US)

(73) Assignee: Yulex Corporation, Maricopa, AZ (US)

( * ) Notice: Subject to any disclaimer, the term of this patent is extended or adjusted under 35 U.S.C. 154(b) by 547 days.

(21) Appl. No.: 11/960,678

(22) Filed: Dec. 19, 2007

(65) Prior Publication Data

US 2009/0163689 A1    Jun. 25, 2009

(51) Int. Cl.  
*C08G 83/00* (2006.01)

(52) U.S. Cl.  
USPC .............................. 528/1; 525/331.9; 525/375

(58) Field of Classification Search ........................ 528/1  
See application file for complete search history.

(56) References Cited

U.S. PATENT DOCUMENTS 2,867,849 A * 1/1959 Drew et al. ................... 264/233  
3,791,838 A * 2/1974 Kaplan ...................... 106/205.1  
4,960,829 A * 10/1990 Allen et al. .................... 525/193  
6,875,391 B2   4/2005 Modha et al.  
7,294,678 B2  11/2007 McGlothlin et al.  
2006/0253956 A1 11/2006 Lipinski

OTHER PUBLICATIONS

International Search Report and Written Opinion dated Apr. 24, 2008, for application PCT/US07/89222 filed on Dec. 31, 2007.

* cited by examiner

*Primary Examiner* — Shane Fang  
(74) *Attorney, Agent, or Firm* — The Law Office of Jane K. Babin, Professional Corporation; Jane K. Babin (57) ABSTRACT

The present disclosure provides for a formula and process for making elastomeric rubber thin film articles. In particular, the formula and process is a system which produces non-*Hevea* or Guayule natural rubber latex (GNRL) thin film articles which have a thickness of 30-80 microns (0.03-0.08 mm), and preferably less than 40 microns (0.04 mm). These thin film articles exhibit physical strength properties similar to that of *Hevea brazilensis* natural rubber latex (NRL). More specifically, the disclosed thin rubber thin film articles exhibit unaged tensile strength of at least 24 MPa (about 3500 psi) and aged tensile strength of at least 19 MPa (about 2800 psi).

13 Claims, 6 Drawing Sheets

GUAYULE NATURAL RUBBER LATEX THIN FILM ARTICLES

FIELD OF THE INVENTION

This invention relates in general to a formula and process for making elastomeric rubber thin film articles, an particularly to a system which produces non-*Hevea* or Guayule natural rubber latex (GNRL) thin film articles which have a thickness of 30-80 microns (0.03-0.08 mm), and the films and articles produced from that process.

BACKGROUND OF THE INVENTION

Natural rubber, derived from the plant *Hevea brasiliensis*, is a core component of many industrial products such as in coatings, films, and packaging. Natural rubber is also used widely in medical devices and consumer items. However, the widespread use of *Hevea* natural rubber is problematic for several reasons. First, the vast majority of *Hevea*-derived natural rubber is grown from a limited number of cultivars in Indonesia, Malaysia and Thailand, using labor-intensive harvesting practices. The rubber and products made from *Hevea* are expensive to import to other parts of the world, including the United States, and supply chains can limit availability of materials. Furthermore, because of the restricted growing area and genetic similarity of these crops, plant blight, disease, or natural disaster has the potential to wipe out the bulk of the world's production in a short time.

Second, particularly in the medical and patient care areas, an estimated 20 million Americans have allergies to proteins found in the Southeast Asian *Hevea*-derived natural rubber crop. Like many other plants, *Hevea* produces proteins for structural support and for defense-related purposes in response to environmental conditions. However, there are at least 62 known *Hevea* antigens involved in Type I latex allergy, and more than a dozen of these *Hevea*-derived latex proteins are common human allergens, including: Hev b1, and Hev b3 used in rubber biosynthesis, defense related proteins Hev b2, Hev b4, Hev b6.01, Hev b6.02, Hev b6.03, Hev b7.01, Hev b7.02, Hev b11, and Hev b12, and other proteins such as Hev b5, Hev b8, Hev b9, and Hev b10.

An allergic response to *Hevea* begins when a latex-allergic individual is exposed to these proteins, triggering immunoglobulin E ("IgE") antibody production. The IgE antibodies cause a variety of responses, depending on the severity of the allergy. Typically, latex allergies are limited to skin inflammation, but serious reactions, and even death, may occur in some individuals.

Overall, the widespread pervasiveness of latex allergies in the U.S. population is costly, particularly in the medical area. To avoid unnecessary allergic reactions during medical procedures, providers must ensure that only alternative latex products come into contact with a latex-allergic patient. Furthermore, practitioners who themselves have latex allergies must ensure that they do not come into contact with natural latex-based products. Finally, synthetic rubber alternatives are often much more expensive or are unavailable in non-*Hevea* latex forms.

DETAILED DESCRIPTION

The present disclosure provides for a formula and process for making elastomeric rubber thin film articles. In particular, the formula and process is a system which produces non-*Hevea* or Guayule natural rubber latex (GNRL) thin film articles which have a thickness of 30-80 microns (0.03-0.08 mm), and preferably less than 40 microns (0.04 mm). These thin film articles exhibit physical strength properties similar to that of *Hevea brazilensis* natural rubber latex (NRL). More specifically, the disclosed thin rubber thin film articles exhibit unaged tensile strength of at least 24 MPa (about 3500 psi) and aged tensile strength of at least 19 MPa (about 2800 psi).

The present disclosure of the process also provide for the cure time, cure temperature, leach time, and leach temperature of a thin film elastomeric material. The present disclosure also provides for the products made from the thin film elastomeric material including, but are not limited to, condoms, tracheal tube cuffs, gloves, catheters, laboratory testing equipment, assays, disposable kits, drug containers, syringes, valves, seals, ports, plungers, forceps, droppers, stoppers, bandages, dressings, examination sheets, wrappings, coverings, tips, shields, and sheaths for endo-devices, solution bags, balloons, thermometers, spatulas, tubing, binding agents, transfusion and storage systems, needle covers, tourniquets, tapes, masks, stethoscopes, medical adhesive, and latex wound-care products.

Guayule (*Parthenium argentatum*) is a desert shrub native to the southwestern United States and northern Mexico and which produces polymeric isoprene essentially identical to that made by *Hevea* rubber trees (e.g., *Hevea brasiliensis*) in Southeast Asia. Guayule normally yields one half ton to one ton of rubber per acre in cultivation when, after two years, the entire plant is harvested and processed. Guayule plants store latex in tiny inclusions in the bark, making harvest of the outer fibrous layers, or bagasse, of the plant, desirable.

Although the present disclosure is applicable and discloses a formula and process for making natural rubber latex thin film articles from many plant species, the production of such articles from guayule is provided here as an exemplar of the novelty and usefulness of this process. Other plant species that can be used include, but are not limited to, gopher plant (*Euphorbia lathyris*), mariola (*Parthenium incanum*), rabbitbrush (*Chrysothamnus nauseosus*), candelilla (*Pedilanthus macrocarpus*), Madagascar rubbervine (*Cryptostegia grandiflora*), milkweeds (*Asclepias syriaca, speciosa, subulata*, et al.), goldenrods (*Solidago altissima, graminifolia, rigida*, et al.), Russian dandelion (*Taraxacum kok-saghyz*), mountain mint (*Pycnanthemum incanum*), American germander (*Teucreum canadense*), and tall bellflower (*Campanula americana*). Many other plants which produce rubber and rubber-like hydrocarbons are known, particularly among the Asteraceae (Compositae), Euphorbiaceae, Campanulaceae, Labiatae, and Moraceae families. All of these non-*Hevea* natural rubber sources are capable of being used in the disclosed process to make thin film materials.

Because non-*Hevea* or guayule natural rubber latex (GNRL) falls into the niche between *Hevea* natural rubber latex (NRL) in terms of physical performance & user comfort and synthetic polyisoprene's poorer physical performance, but lacks the type I antigenic cross-reactivite proteins, GNRL compounded using the below-described formulations allows a combination of the most favorable aspects of both rubber types.

According to the present disclosure, the non-*Heava* or Guayule latex is compounded as described below, in one of two alternate formulations, with PHR meaning parts per hundred resin or polymer. The first formulation is shown in Table 1 below.

TABLE 1

| Formulation I | PHR |
|---|---|
| Non-*Heava* latex KOA or HA | 100 |
| Ammonium Hydroxide | 1.0 |
| Wingstay L Antioxidant Dispersion | 2.0 |
| Zinc Oxide Dispersion | 1.00 |
| TBBS | 0.6 |
| ZDEC | 0.5 |
| DPG | 0.4 |
| Sulfur Dispersion | 2.0 |
| $H_2O$ top up to 36-53% total solid contents (depend on dipping desire total solid content (TSC)) | |
| Swell % requirement prior to dip | 120-170 |

An alternate formulation according to the present disclosure is shown in Table 2 below.

TABLE 2

| Formulation II | PHR |
|---|---|
| Non-*Hevea* Latex KOA or HA | 100 |
| Ammonium Hydroxide | 1.0 |
| Wingstay L Antioxidant Dispersion | 2.0 |
| Titanium Dioxide Dispersion | 0.5 |
| Zinc Oxide Dispersion | 1.00 |
| TBBS | 0.6 |
| ZDEC | 0.5 |
| DPG | 0.4 |
| Sulfur Dispersion | 2.0 |
| $H_2O$ top up to 36-53% total solid contents (depend on dipping desire total solid content (TSC)) | |
| Swell % requirement prior to dip | 120-170 |

The dithiocarbamate compound for use in the present disclosure is zinc diethyldithiocarbamate, also known as ZDEC or ZDC. Suitable ZDEC for use includes Bostex™ 561 (commercially available from Akron Dispersions, Akron, Ohio). The guanidine compound used in the accelerator composition is diphenyl guanidine, also known as DPG. Suitable DPG which can be used includes Bostex™ 417 (commercially available from Akron Dispersions, Akron, Ohio). The sulfenamide compound used in the accelerator composition is t-butylbenzothiazole sulfenamide, also known as TBBS. Suitable TBBS for use includes 50% BBTS (available from Akron Dispersions, Akron, Ohio).

The non-*Hevea* latex is compounded by first measuring the total solids content (TSC) of the non-*Hevea* latex and each additive specified above and apply to the formulation. Second, pour the latex into container and turn mixer/stirrer on. Ensure all chemical dispersions have been well mixed prior to addition. Follow the order of addition per the tables above, depending on which on the two alternate formulations are used, allowing 1-2 minutes mixing in between each chemical addition. After addition of the final compound ingredient, continue mixing the compound for an additional 20-minutes minimum. Put the compounded latex into a water bath or an oven at 38-40 degrees Celsius (C) for 15 hours (prevulcanization time). After the prevulcanization time has elapsed, chill the compound to nominally 25° C.

Optionally, the compounded latex can be vulcanized at the room temperature from 24-96 hrs or until the swell meets the specification below. Finally, perform the modified toluene swell test as described below.

Modified toluene swell test method. To perform the modified swell test, pour 0.75 ml of 5% aqueous $CaCO_3$ solution into either an aluminum or a polypropylene weighing dish and dry it either in a 65° C. oven or air dry at ambient temperature. Cool to room temperature, if oven dried, and add 1.5 ml of compounded latex. Gently swirl latex to form a uniform layer and air dry. Complete dryness is indicated when the film turns from opaque white to translucent amber. Optionally, the latex film can be dried in a 60° C. oven for 15 minutes.

Coat the top surface of the film with $CaCO_3$ powder to prevent the surface of the film from sticking to itself. Peel the film out of the weighing dish. Use a 25 mm circle die to cut a 25 mm film. Put it into a covered Petri dish containing toluene (10 mm height from the base of the Petri dish) for 15 minutes. Hand swirl the Petri dish every 3-5 mins. to prevent the film from sticking to the Petri dish bottom. After 15 minutes, measure the final diameter of the film through the base of the dish.

Finally, perform the Linear Swell % calculation using the following Formula 1:

Linear Swell %=[(final diameter−initial diameter)/initial diameter]×100, with the Initial diameter=25 mm.     Formula 1.

The Linear Swell % meets specification at 80-170%. After swell % has been found to meet the specification, transfer the latex into the dipping container, and dipping may begin thereafter. Optionally, after swell % has been found to meet the specification the latex can be centrifuged in the centrifuge or the clarifier to remove unnecessary react chemical then transfer the latex into the dipping container, and dipping may begin thereafter. The can be kept in the ambient temperature condition during the dipping and/or storage If should be noted that the non-*Hevea* latex should be kept in a cool location (refrigerator preferred) if dipping is not expected to take place for some time. The latex compound has been found to last up to 30 days or more so long as it is kept moderately cool (10° C.-25° C.). The extra latex from the compounding can be kept in the cool condition and top up over time, depending on the consumption.

The thin film article is then produced using the above compounded latex, according to one of the alternate processes disclosed in FIG. 1, FIG. 2, or FIG. 3, discussed in further detail below to form the desired thin film materials. The dipping process can be either a straight dip or coagulant dip. The straight dip will utilize a 2-dip process, which dip into a Guayule latex solution of total solids content (TSC) range from 36-53% (preferably 50%). On the other hand, the coagulant dip will be a single dip process, which dip into a Guayule latex solution of total solids content (TSC) range from 15-25%; preferably 20%. However, the single dip process will utilize a coagulant dipping, where the coagulant TSC range from 5-15%; preferably 10%, prior to latex dip.

Figure 1:
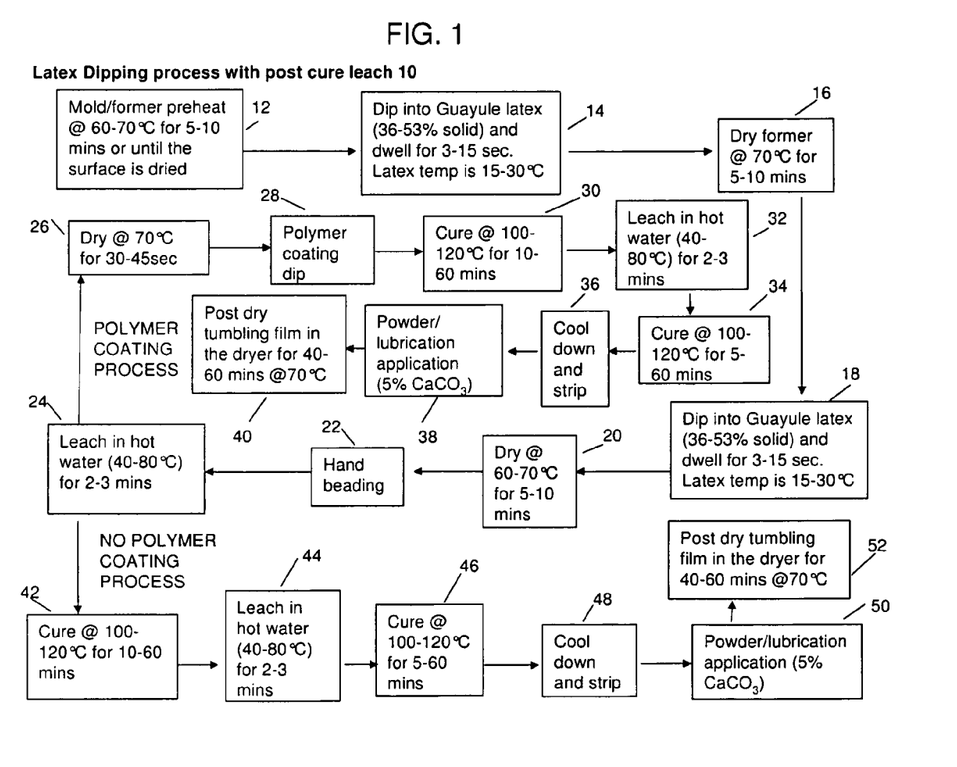
FIG. 1 is a flowchart illustrating the latex dipping process with post cure leach.

According to FIG. 1, the article is made using latex dipping process 10 with post cure leach. In coagulant dipping process 10, the mold or former for the desired article, e.g. condom, is first preheated in step 12 at 60-70° C. for about five to ten minutes or until the surface is dried. Next, in step 14, the mold is dipped into the non-*Hevea* latex, prepared as described above with approximate 36-53% solid content, and dwelled for three to fifteen seconds. In step 12, the latex temperature should be about 15-30° C. In step 16, the mold is dried at 70° C. for about five to ten minutes. Then, in step 18, the mold is again dipped into the non-*Hevea* latex, prepared as described above with approximately 36-53% solid content, and dwelled for three to fifteen seconds. In step 18, the latex temperature should be about 15-30° C. In step 20, the mold is dried at 70° C. for about five to ten minutes. In step 22, the latex is hand-beaded as required by the desired thin film article being form from the latex. Next, in step 24, the latex-covered mold is leached in hot (about 40°-80° C.) water for two to three minutes.

If it is desired to polymer coat the thin film article, proceed through the polymer coating process in steps 26-40. In step 26, dry the latex-covered mold at 70° C. for about 30-45 seconds. In step 28, dip in polymer coating and then in step 30, cure at 100-120° C. for 10-60 minutes. Then in step 32, leach in hot (about 40°-80° C.) water for two to three minutes. In step 34, cure again at 100-120° C. for 5-60 minutes, and then cool down and strip the thin film article from the mold in step 36. If powder or lubrication is desired, apply this in step 38 (e.g. 5% $CaCO_3$). Then, in step 40, perform post dry tumbling of the thin film article in the dryer for 40-60 minutes at 70° C.

If no polymer coating process is used, the proceed to steps 42-52, and in step 42, cure the latex-covered mold at 100-120° C. for 10-60 minutes, and then leach in hot (about 40°-80° C.) water for two to three minutes, in step 44. In step 46, cure again at 100-120° C. for 5-60 minutes, and then cool down and strip the thin film article from the mold in step 48. If powder or lubrication is desired, apply this in step 50 (e.g. 5% $CaCO_3$). Then, in step 52, perform post dry tumbling of the thin film article in the dryer for 40-60 minutes at 70° C.

Figure 2:
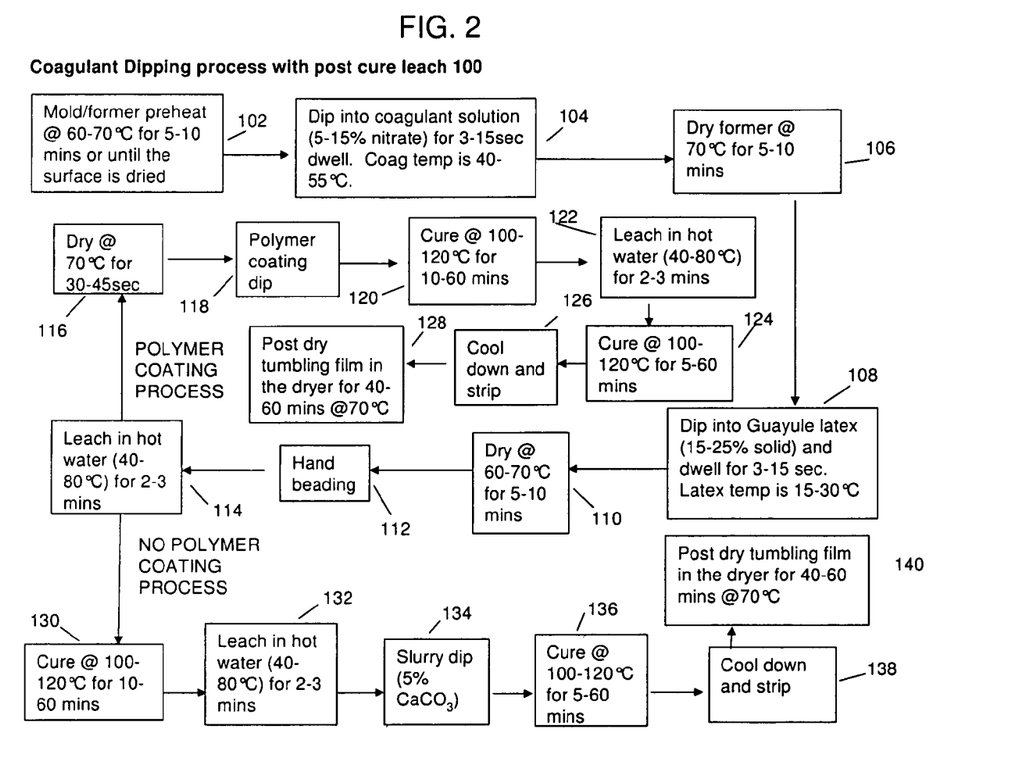
FIG. 2 is a flowchart illustrating the coagulant dipping process with post cure leach.

In an alternate embodiment shown in FIG. 2, the article is made using coagulant dipping process 100 with post-cure leach. In coagulant dipping process 100, the mold or former for the desired article, e.g. condom, is first preheated in step 102 at 60-70° C. for about five to ten minutes or until the surface is dried. Next, in step 104, the mold is dipped into a coagulant solution of about 5-15% nitrate and dwelled for three to fifteen seconds. The coagulant temperature in step 104 should be about 40-55° C. In step 106, the mold is dried at 70° C. for about five to ten minutes. Then, in step 108 the mold is dipped into the non-*Hevea* latex, prepared as described above with approximately 15-25% solid content, and dwelled for three to fifteen seconds. In step 108, the latex temperature should be about 15-30° C. In step 110, the mold is dried at 70° C. for about five to ten minutes. In step 112, the latex is hand-beaded as required by the desired thin film article being form from the latex. Next, in step 114, the latex-covered mold is leached in hot (about 40°-80° C.) water for two to three minutes.

If it is desired to polymer coat the thin film article, proceed through the polymer coating process in steps 116-128. In step 116, dry the latex-covered mold at 70° C. for about 30-45 seconds. In step 118, dip in polymer coating and then in step 120, cure at 100-120° C. for 10-60 minutes. Then in step 122, leach in hot (about 40°-80° C.) water for two to three minutes. In step 124, cure again at 100-120° C. for 5-60 minutes, and then cool down and strip the thin film article from the mold in step 126. Then, in step 128, perform post dry tumbling of the thin film article in the dryer for 40-60 minutes at 70° C.

If no polymer coating process is used, the proceed to steps 130-140, and in step 130, cure the latex-covered mold at 100-120° C. for 10-60 minutes, and then leach in hot (about 40°-80° C.) water for two to three minutes, in step 132. In step 134, perform a slurry dip (e.g. 5% $CaCO_3$) and cure again at 100-120° C. for 5-60 minutes in step 136, and then cool down and strip the thin film article from the mold in step 138. Then, in step 140, perform post dry tumbling of the thin film article in the dryer for 40-60 minutes at 70° C.

Figure 3:
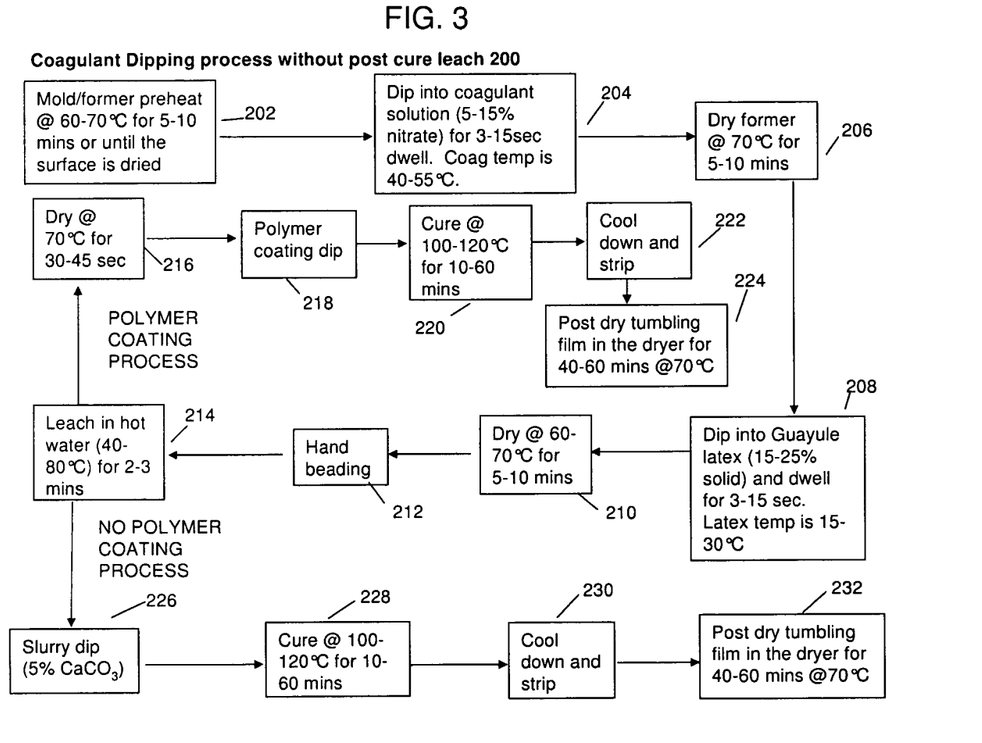
FIG. 3 is a flowchart illustrating the coagulant dipping process without post cure leach.

FIG. 3 illustrates a further embodiment of the disclosed process, namely coagulant dipping process 200, without post-cure leach. In coagulant dipping process 200, the mold or former for the desired article, e.g. condom, is first preheated in step 202 at 60-70° C. for about five to ten minutes or until the surface is dried. Next, in step 204, the mold is dipped into a coagulant solution of about 5-15% nitrate and dwelled for three to fifteen seconds. The coagulant temperature in step 204 should be about 40-55° C. In step 206, the mold is dried at 70° C. for about five to ten minutes. Then, in step 208 the mold is dipped into the non-*Hevea* latex, prepared as described above with approximate 36-53% solid content, and dwelled for three to fifteen seconds. In step 108, the latex temperature should be about 15-30° C. In step 210, the mold is dried at 60-70° C. for about five to ten minutes. In step 212, the latex is hand-beaded as required by the desired thin film article being form from the latex. Next, in step 114, the latex-covered mold is leached in hot (about 40°-80° C.) water for two to three minutes.

If it is desired to polymer coat the thin film article, proceed through the polymer coating process in steps 216-224. In step 216, dry the latex-covered mold at 70° C. for about 30-45 seconds. In step 218, dip in polymer coating, and then in step 220, cure at 100-120° C. for 10-60 minutes. Cool down and strip the thin film article from the mold in step 222. Then, in step 224, perform post dry tumbling of the thin film article in the dryer for 40-60 minutes at 70° C.

If no polymer coating process is used, the proceed to steps 226-232, and in step 226, perform a slurry dip (e.g. 5% $CaCO_3$) and cure again at 100-120° C. for 5-60 minutes in step 228, and then cool down and strip the thin film article from the mold in step 230. Then, in step 232, perform post dry tumbling of the thin film article in the dryer for 40-60 minutes at 70° C.

As noted above, the non-*Hevea* thin film articles can be with powdered or powder free. For the powder free articles, an additional backend process can be incorporated to remove the powder from the articles. If no polymer coating was applied above, no coating chlorination process 300, shown in FIG. 4, can be used; whereas if a polymer coating was applied above, polymer coating chlorination process 400, shown in FIG. 5, can be used.

Figure 4:
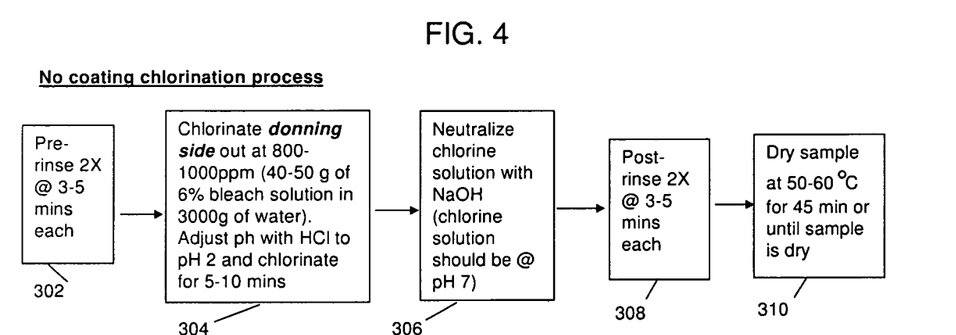
FIG. 4 is a flowchart illustrating the no coating chlorination process.

As shown in FIG. 4, in no coating chlorination process 300, a pre-rinse of the thin film article is performed twice (repeat step 302 once), each pre-rinse lasting three to five minutes. In step 304, the thin film article is chlorinated with the donning side out at 800-1000 ppm (part per million). Thus, a solution comprised of 40-50 grams of 6% bleach solution in 3000 g of water can be used. The optimum pH for chlorination according to the present disclosure is approximately 2, and the above chlorine solution can be adjusted with hydrochloride (HCl) to lower the pH to 2, if needed. Chlorination in step 304 should be performed for five to ten minutes. In step 306, neutralize the chlorine solution with sodium hydroxide (NaOH) until the chlorine solution reaches a pH of about 7. Then in step 308, perform a post-rinse twice (repeat step 308 once), each post-rinse lasting three to five minutes. Finally, in step 310, dry the thin film article at 50-60° C. for about 45 minutes or until the thin film article is dry.

Figure 5:
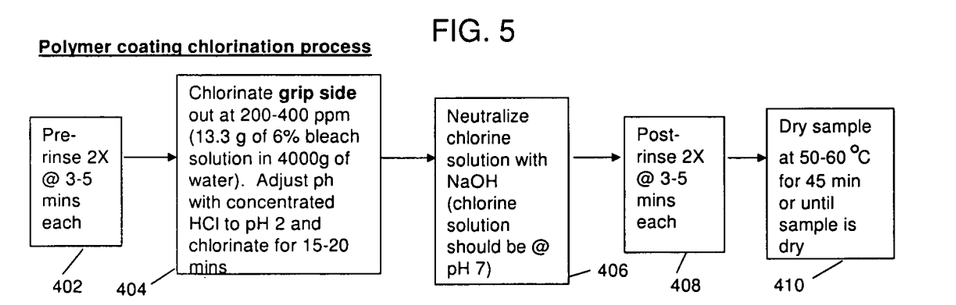
FIG. 5 is a flowchart illustrating the polymer coating chlorination process.

As shown in FIG. 5, in the polymer coating chlorination process 400, a pre-rinse of the thin film article is performed twice (repeat step 402 once), each pre-rinse lasting three to five minutes. In step 404, the thin film article is chlorinated with the grip side out at 200-400 ppm (part per million). Thus, a solution comprised of approximately 13.3 grams of 6% bleach solution in 4000 g of water can be used. The optimum pH for chlorination according to the present disclosure is approximately 2, and the above chlorine solution can be adjusted with hydrochloride (HCl) to lower the pH to 2, if needed. Chlorination in step 304 should be performed for ten to fifteen minutes. In step 406, neutralize the chlorine solution with sodium hydroxide (NaOH) until the chlorine solution reaches a pH of about 7. Then in step 408, perform a post-rinse twice (repeat step 308 once), each post-rinse lasting three to five minutes. Finally, in step 410, dry the thin film article at 50-60° C. for about 45 minutes or until the thin film article is dry.

The non-*Hevea* natural rubber thin film articles produced according to the above process have a thickness of 30-80 microns (0.03-0.08 mm), and preferably less than 40 microns (0.04 mm). These thin film articles exhibit physical strength properties similar to that of *Hevea brazilensis* natural rubber latex (NRL). According to the present disclosure, the disclosed thin rubber thin film articles exhibit unaged tensile strength of at least 24 megapascals (MPa) (about 3500 pounds per square inch (psi)) and aged tensile strength of at least 19 MPa (about 2800 psi).

As a result of a combination of the polymer architecture, the compound formulation and the production process, thin films produced from non-*Hevea* or guayule natural rubber latex (GNRL) reliably tend to be at least 50% lower in Modulus versus comparably compounded *Hevea* natural rubber latex (NRL). Modulus is a measure of the force required to stretch a sample to a given percent elongation and correlates to softness—the lower the modulus the softer the film. In addition, the elongation will be 5-15% higher as compared to the NRL and/or other synthetic elastomers. Elongation at break is a measure of how far the sample can stretch until the point of rupture.

Figure 6:
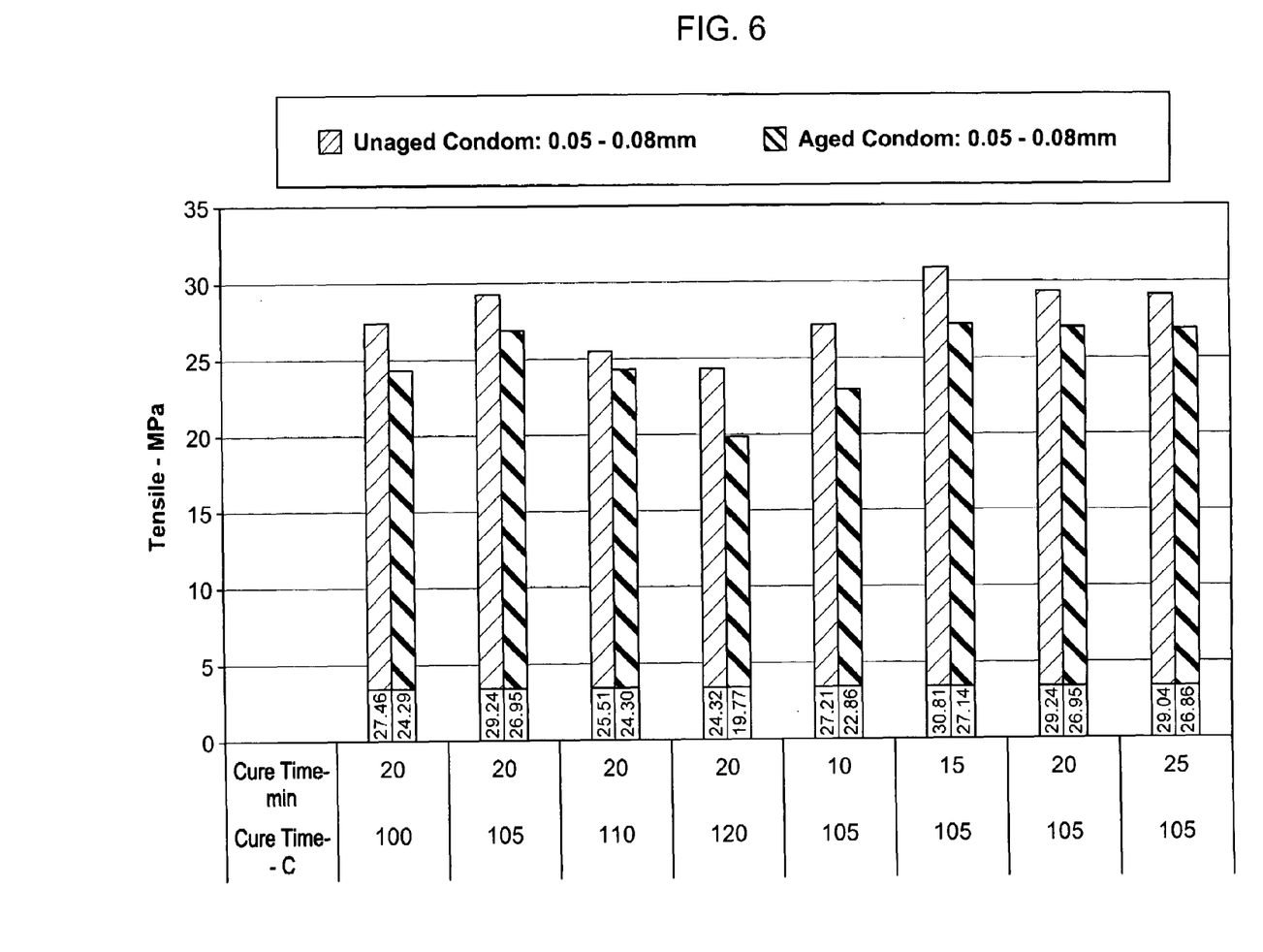
FIG. 6 is a graph illustrating tensile strength of unaged and aged thin film material with various cure times and cure temperatures.

Last, the unaged tensile strength results will yield at least 24 MPa (about 3500 psi) and the aged tensile strength of at least 19 MPa (about 2800 psi). Tensile strength is a measure of the force at break divided by the cross sectional area of the sample specimen test area at the point of rupture. More specifically, in one example shown in FIG. 6, the unaged tensile strength of ultra-thin condoms with a thickness of 50-80 microns (one example of a thin film article disclosed herein) ranged from 24.32-30.81 MPa (3526-4467 psi) and the aged tensile strength of ultra-thin condoms ranged from 19.77-27.14 MPa (2867-3935 psi). The aged articles were aged in the oven at 70° C. for 7 days as specified by ASTM D 573. Testing of both unaged and accelerated aged physical properties were performed in accordance with ASTM D 412.

Figure 7:
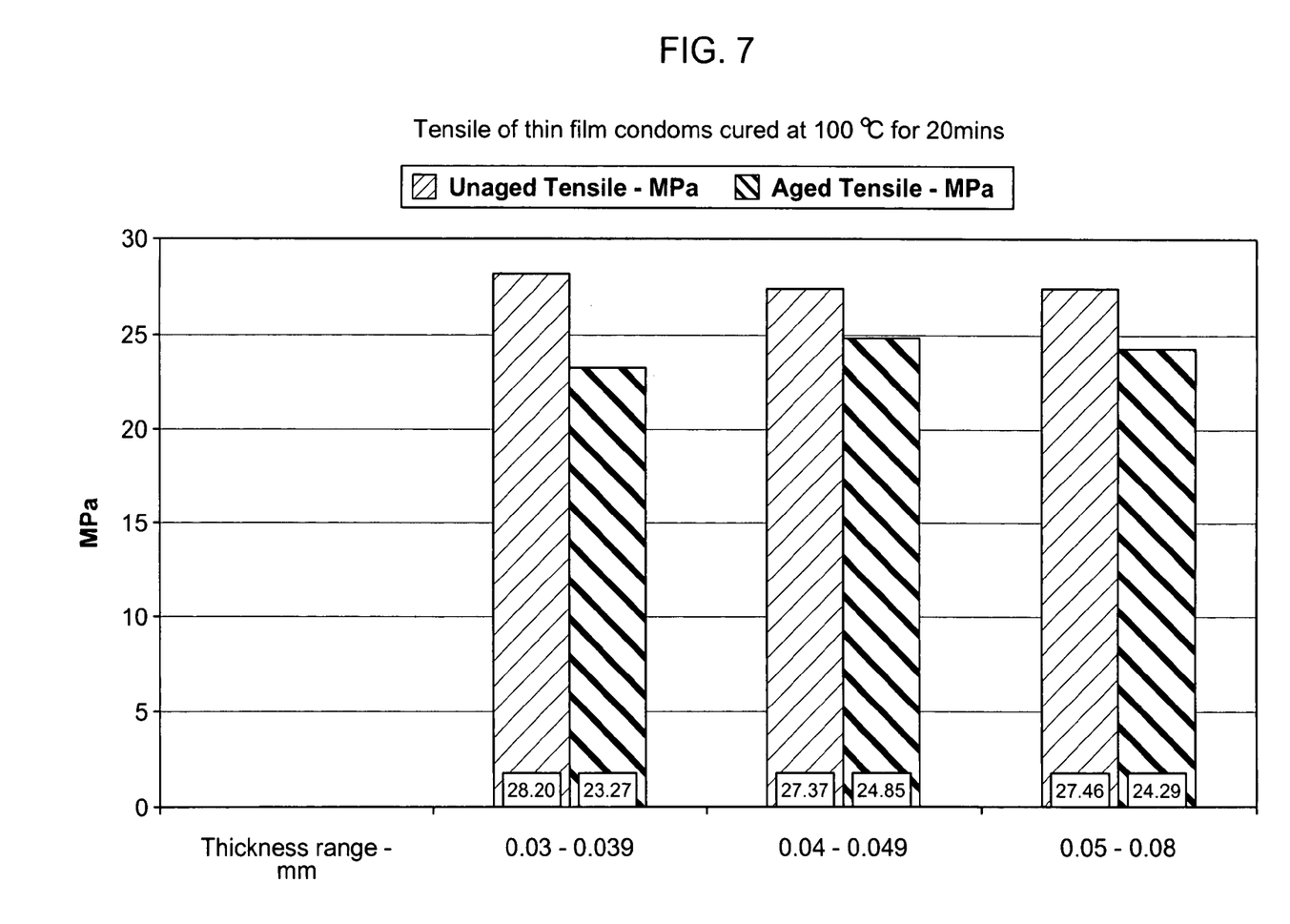
FIG. 7 is a graph illustrating the tensile strength of think film material cured at 100° C. for 20 minutes.

FIG. 7 further illustrates another example of the tensile strength of the disclosed thin film materials at various thicknesses. The tensile strength of the ultra-thin condoms with a thickness of 30-40 microns ranged from over 28 MPa for unaged condoms and over 23 MPa for aged condoms. The tensile strength of the ultra-thin condoms with a thickness of 40-50 microns ranged from over 27 MPa for unaged condoms and over 24 MPa for aged condoms. The tensile strength of the ultra-thin condoms with a thickness of 50-80 microns ranged from over 27 MPa for unaged condoms and over 24 MPa for aged condoms The formulation and process described above allow production of thin film articles which yield high product performance, having desirable properties equal to or better than that of *Hevea* natural rubber but without the presence of *Hevea* natural rubber latex proteins and allergens. Another advantage of the disclosed process is that conventional manufacturing equipment and most readily-available materials can be used in accordance with the invention to make a surgical glove, for example, without the need for new or costly additional materials or equipment. Further, no complicated new process steps are required by the invention and the invention can be readily incorporated into existing glove making processes and systems.

The compounded (or ready to use) GNRL composition formulated in accordance with the invention exhibits prolonged storage stability. For example, the pre-cure storage stability of the compounded GNRL composition (i.e., the time period between the completion of compounding and use of the latex composition in the dipping and curing stages) can be extended up to about 7 days, in contrast to the typical current 3 to 5 day time period. By extending storage life of the latex, the amount of wasted latex can be significantly reduced and greater flexibility in scheduling manufacturing processes is permitted. Further, unlike classic accelerators, the accelerators used in the present disclosure are either low or non-nitrosamine generating. This is advantageous as nitrosamines are known potential carcinogens.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of a preferred embodiment and best mode of the invention known to the applicants at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

What is claimed is:

1. A process for manufacturing a non-*Hevea* natural rubber latex thin film article, comprising:
   a. compounding non-*Hevea* natural rubber latex, wherein compounding consists of mixing the non-*Hevea* natural rubber latex with ammonium hydroxide, an antioxidant dispersion, a zinc oxide dispersion, a dithiocarbamate compound, a sulfonamide compound, a guanidine compound, a sulfur dispersion, optionally a titanium dioxide dispersion, and optionally $H_2O$, wherein the compounded non-*Hevea* natural rubber latex has a linear swell percentage ranging from eighty to one hundred seventy percent;
b. dipping a mold for a thin film article in the compounded latex, forming a thin film consisting of the compounded latex on the mold;
c. curing the thin film consisting of the compounded latex on the mold at a temperature in the range of one-hundred to one hundred twenty degrees Celsius; and
d. removing the thin film from the mold after the thin film on the mold has cooled, thereby producing a thin film article with a thickness of less than about eighty microns.

2. The process of claim 1, wherein the non-*Hevea* natural rubber latex is derived from guayule.

3. The process of claim 1, wherein the linear swell percentage ranges from one hundred twenty to one hundred seventy percent prior to dipping.

4. The process of claim 1, wherein the compounded non-*Hevea* natural rubber latex comprises total solid contents in the range of about thirty-five to fifty-five percent.

5. The process of claim 1, wherein the dithiocarbamate compound is zinc diethyldithiocarbamate.

6. The process of claim 1, wherein the guanidine compound is diphenyl guanidine.

7. The process of claim 1, wherein the sulfonamide compound is t-butylbenzothiazole sulfenamide.

8. The process of claim 1, further including dipping the mold into a coagulant solution prior to dipping the mold in the compounded latex.

9. The process of claim 1, further including performing a post-cure leach prior to removing the thin film from the mold.

10. The process of claim 1, further including post dry tumbling the thin film article at a temperature of approximately seventy degrees Celsius.

11. The process of claim 1, further including dipping the thin film on the mold into a polymer coating prior to curing the thin film on the mold.

12. The process of claim 1, further including chlorinating the thin film article donning side out after removing the thin film article from the mold.

13. The process of claim 11, further including chlorinating the thin film article grip side out after removing the polymer coated thin film article from the mold.

* * * * *